United States Patent [19]

Hansen, Jr. et al.

[11] Patent Number: 4,767,744
[45] Date of Patent: Aug. 30, 1988

[54] SUBSTITUTED TYROSYL METHIONYL DIPEPTIDE AMIDES

[75] Inventors: Donald W. Hansen, Jr., Chicago; Daniel R. Pilipauskas, Glenview; Michael Clare, Skokie, all of Ill.

[73] Assignee: G. D. Searle & Co., Chicago, Ill.

[21] Appl. No.: 14,329

[22] Filed: Feb. 13, 1987

Related U.S. Application Data

[63] Continuation-in-part of Ser. No. 882,796, Jul. 14, 1986, which is a continuation-in-part of Ser. No. 829,398, Feb. 14, 1986, abandoned, which is a continuation-in-part of Ser. No. 765,885, Aug. 14, 1985, abandoned.

[51] Int. Cl.[4] ............ A61K 37/02; C07K 5/06; C07C 103/20; C07D 207/00
[52] U.S. Cl. ............ 514/19; 530/302; 564/157; 514/616; 514/423; 548/537; 548/538
[58] Field of Search ............ 530/302; 514/19, 616, 514/423; 548/537, 538; 564/157

[56] References Cited

U.S. PATENT DOCUMENTS

| | | | |
|---|---|---|---|
| 4,127,535 | 11/1978 | Coy et al. | 530/302 |
| 4,316,892 | 2/1982 | Jones | 530/302 |
| 4,407,746 | 10/1983 | Mazur et al. | 530/302 |
| 4,579,841 | 4/1986 | Stewart et al. | 514/19 |
| 4,603,121 | 7/1986 | Hansen, Jr. et al. | 530/302 |

Primary Examiner—Delbert R. Phillips
Attorney, Agent, or Firm—Frank P. Grassler; J. Timothy Keane; Paul D. Matukaitis

[57] ABSTRACT

This invention relates to novel substituted tyrosyl alanine dipeptide amides of the formula:

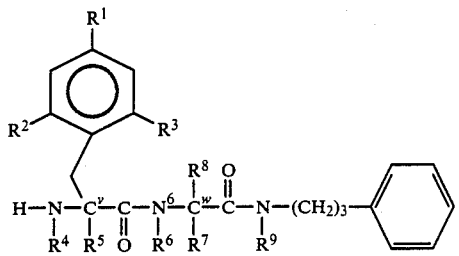

and the pharmaceutically acceptable addition salts thereof, wherein $R^1$ is —OH, —OCH$_3$ or lower alkoxy of 1-6 carbon atoms; wherein $R^2$ and $R^3$ may be the same or different and represent straight or branched chain lower alkyl of 1-6 carbon atoms; wherein $R^4$, $R^5$ $R^9$ may be the same or different and represent hydrogen or straight or branched chain lower alkyl having 1-6 carbon atoms; wherein $R^6$ represents hydrogen, or straight or branched chain lower alkyl of 1-6 carbon atoms, or $R^6$ may act together with $N^6$, $C^w$ and either $R^7$ $R^8$ to form a cycloamine of the formula:

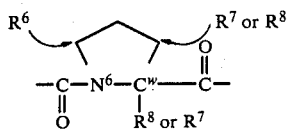

such that between $R^7$ and $R^8$, when one acts to form said cycloamine, the other is hydrogen, or straight or branched chain lower alkyl of 1-6 carbon atoms; wherein when neither $R^7$ nor $R^8$ is acting to form said cycloamine, $R^7$ $R^8$ act together with $C^w$ to form a cycloalkyl of the formula:

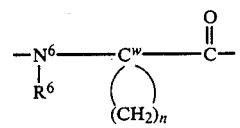

where n=3, 4, 5; wherein $C^w$ represents an asymmetric carbon atom when $R^7$ and $R^8$ are not the same and may be racemic or have the D or L configuration; and wherein $C^v$ represents an asymmetric carbon atom that may be racemic or that may hve the D or L configuration.

These compounds are useful because they possess analgesic activity in mammals.

10 Claims, No Drawings

SUBSTITUTED TYROSYL METHIONYL DIPEPTIDE AMIDES

This application is a continuation-in-part of pending Ser. No. 882,796, filed July 14, 1986, which is a continuation-in-part of Ser. No. 829,398, filed Feb. 14, 1986, now abandoned, which is a continuation-in-part of Ser. No. 765,885, filed Aug. 14, 1985, also now abandoned.

BACKGROUND OF THE INVENTION

1. Field of the Invention

The present invention relates to novel substituted tyrosyl dipeptide amides. In particular, it provides novel tyrosyl dipeptide amides of Formula I which are useful as analgesic agents.

2. Prior Art

In 1975, a pentapeptide, methionine enkephalin, was reported by Hughes et al., *Nature*, 258, 577 (1975). This peptide is found in many areas of the brain where it appears to act as a neurotransmitter or neuromodulator in a central pain-suppressant system. This naturally occurring peptide binds stereospecifically to partially purified brain opiate receptor sites. See for example Bradberry et al., *Nature*, 260, 793 (1976). It is also highly active in bioassays for opiate activity but exhibits only weak, fleeting analgesic activity when injected directly into the brain of the rat. See for example Belluzi et al., *Nature*, 260, 625 (1976).

In order to overcome the lack of in vivo activity, a number of investigators have made numerous modifications in the methionine enkephalin structure, such as substituting the glycine in the 2-position with a D-amino acid, N-methylation of the L-tyrosine, substituting the 4-phenylalanine with, for example, methyl or halo, modifying the C-terminus, etc., to produce enkephalin derivatives of varying properties and potencies.

Kiso, et al., *Peptide Chemistry* 1981, 65–70, Protein Research Foundation, Osaka, Japan (1982), disclosed the synthesis and activity of short chain enkephalin-like peptides, among them tripeptide and dipeptide alkylamides such as N-methyltyrosine-(D)-methionine sulfoxide-glycine-methylphenethylamine and tyrosine-(D)-methionine sulfoxide-phenylpropylamide.

Vavrek, et al., *Peptides* 2, 303, 1981, disclosed analogs of enkephalin, among them the dipeptide tyrosine-D-alanine-phenylpropylamide, (Tyr-(D)Ala-PPA).

Hansen, et al., U.S. Pat. No. 4,599,325, which issued July 8, 1986 to the inventors of the present invention, discloses tyrosyl dipeptide amides possessing analgesic activity in mammals.

The compounds of this invention have unexpected and surprisingly superior properties when compared to the Vavrek, et al. compounds. The present invention provides new dipeptide derivatives which show improved potency as analgesic agents by both oral and parenteral routes of administration. Additionally, U.S. Pat. No. 4,316,892 relates to certain derivatives of methonine enkephalin derivatives useful as analgesic agents.

SUMMARY OF THE INVENTION

This invention encompasses anagesic tyrosine derivatives of Formula I:

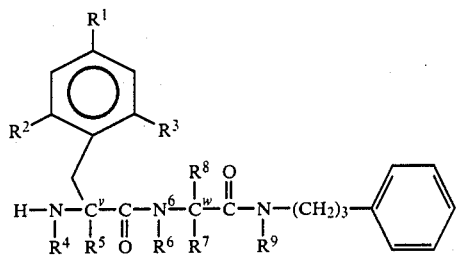

and the pharmaceutically acceptable addition salts thereof, wherein $R^1$ is —OH, —OCH$_3$ or contemplated equivalents including lower alkoxy of 1–6 carbon atoms;

wherein $R^2$ and $R^3$ may be the same or different and represent straight or branched chain lower alkyl of 1–6 carbon atoms;

wherein $R^4$, $R^5$ and $R^9$ may be the same or different and represent hydrogen or straight or branched chain lower alkyl having 1–6 carbon atoms;

wherein $R^6$ represents hydrogen, or straight or branched chain lower alkyl of 1–6 carbon atoms, or $R^6$ may act together with $N^6$, $C^w$ and either $R^7$ or $R^8$ to form a cycloamine of the formula:

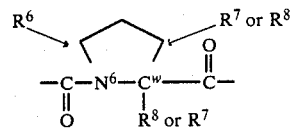

such that between $R^7$ and $R^8$, when one acts to form said cycloamine, the other is hydrogen, or straight or branched chain lower alkyl of 1–6 carbon atoms;

wherein when neither $R^7$ nor $R^8$ is acting to form said cycloamine, $R^7$ and $R^8$ act together with $C^w$ to form a cycloalkyl of the formula:

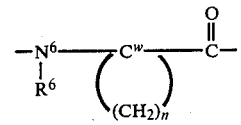

wherein n=3, 4, 5;

wherein $C^w$ represents an asymmetric carbon atom when $R^7$ and $R^8$ are not the same and may be racemic or have the D or L configuration; and wherein $C^v$ represents an asymmetric carbon atom that may be racemic or that may have the D or L configuration.

DETAILED DESCRIPTION

The compounds described in this invention are prepared according to the reaction sequence outlined in Scheme I. In Scheme I, an amino acid derivative (X) of known configuration which has its amino group blocked by "Z," is transformed into a mixed anhydride by reaction with isobutylchloroformate (IBCF) in the presence of N-methylmorpholine (NMM). The mixed anhydride is then coupled to the amino group of 3-phenyl-1-propamine to form am amide linkage. The amino blocking group, t-butoxycarbonyl, (Boc), is then removed by hydrolysis in 6N HCl/dioxane to provide the amino amide (XII). Similarly, a 2,6-dialkyl amino-blocked-D,L-tyrosine derivative (XIII) is transformed into a mixed anhydride by reaction with isobutylchloroformate and N-methyl-morpholine. The resulting mixed anhydride is then coupled with the amino group on the amino amide (XII) to produce a substituted tyrosyl dipeptide amide as a mixture of diastereomers (XIV).

The resulting pair of diastereomers can be separated by methods well known in the art, such as by chromatography, crystallization and the like, to produce the individual diastereomers. The individual diastereomers can then be deblocked by hydrolysis with 6N HCl/dioxane to produce the compounds of Formula I.

In Scheme I, "Boc" refers to the amino blocking group t-butoxy carbonyl; $R^1$ through $R^9$ are as previously defined. The "Z" of compound X represents the amino blocking group "Boc" or benzyloxycarbonyl. In sulfur containing X, the Z is preferably Boc and it can be removed by hydrolysis with 6N HCl/dioxane.

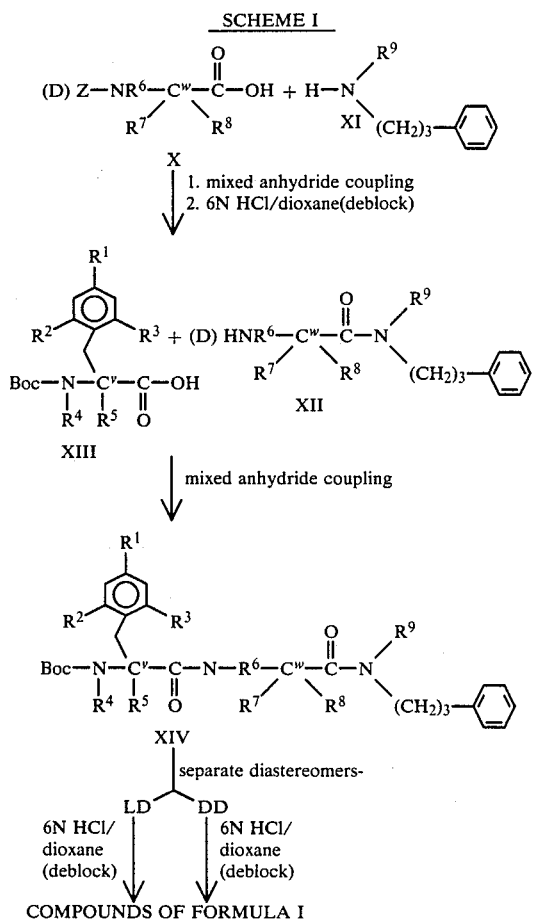

Analogous to the enhanced analgesic properties of tyrosyl dipeptide amides already disclosed in our C.I.P. series of co-pending applications (Ser. No. 882,796, filed July 14, 1986; Ser. No. 827,398, filed Feb. 14, 1986; and Ser. No. 765,885, filed Aug. 14, 1985), the dipeptide amides of the present invention possess unexpectedly superior analgesic activity over the enkephlin-like dipeptides disclosed by Vavrek, et al. More specifically, Ser. No. 881,796, of which this application is a continuation-in-part, discloses enhanced analgesic properties for compounds of the formula:

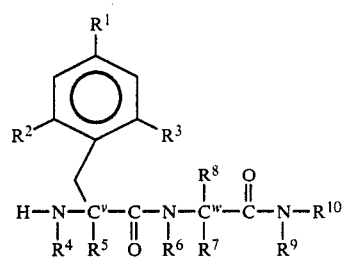

and the pharmaceutically acceptable acid addition salts thereof where $R^1$ is hydrogen, lower alkyl, hydroxy, lower alkoxy, $-O(CH_2)_n$phenyl with the phenyl optionally substituted by halogen, $-NO_2$, $-CN$, $-NH_2$ or lower alkyl wherein n is 1 to 4; $R^2$ and $R^3$ represent lower alkyl, halogen, or lower alkoxy, or either one of $R^2$ or $R^3$ is hydrogen and the other is lower alkyl, lower alkoxy or halogen; $R^4$, $R^5$, $R^6$, and $R^9$ may be the same or different and represent hydrogen, lower alkyl, cycloalkyl having 3 to 8 carbons, unsaturated lower alkyl, or $-(CH_2)_m$cycloalkyl with the cycloalkyl having 3 to 8 carbons and m is 1 to 4; $R^{10}$ is hydrogen or $-(CH_2)_p$-phenyl or with the phenyl optionally substituted with $-NH_2$, $-OH$, halogen, $-NO_2$, or lower alkyl or $-(CH_2)_p$thienyl wherein p is 1 to 4; one of $R^7$ or $R^8$ is $-(CH_2)_f-S(O)_z-(CH_2)_q-CH_3$ where f is 1 to 3 and q is 0 to 3, z is 0, 1 or 2 and the other is hydrogen or lower alkyl, or $R^7$ and $R^8$ together with carbon w is $$C_w \diagup_{(CH_2)_y}^{(CH_2)_x} \diagdown S-O_z$$

where x and y are independently 1 to 3 and z is 0, or 2. V represents an asymmetric carbon that may be racemic or have the D or L configuration; W represents an asymmetric carbon when $R^7$ and $R^8$ are not the same that may be racemic or have the D or L configuration.

The analgesic activity of the compounds of the present invention is demonstrated by their respective activities in the Writhing and Opiate Binding Assays. In some cases, the analgesic activity of the representative compounds was compared with that of a disclosed analog of enkephalin, (L)-tyrosine-(D)-alaninyl-phenylpropylamide.

Writhing Assay

Male Charles River albino mice (CD-1/HAM/1LR) weighing between 20 and 30 grams were used. Thirty minutes after subcutaneous or intragastric administration of a dose (0.1 mg/10 gram body weight) of the test compound, a 0.025% (w/v) phenylbenzoquinone solution was injected intraperitoneally (0.1 ml/10 gram body weight). Five minutes later, each mouse was placed in a large glass beaker and the number of writhes that occurred in the subsequent ten minutes was counted. A writhe consisted of dorsoflexion of the back, extension of the hind limbs, and strong contraction of the abdominal musculature. The test compound was considered to have produced analgesia in a mouse if the number of writhes elicited by phenylbenzoquinone was equal to or less than one-half the median number of writhes recorded for the saline-treated group that day. The results were expressed as the number of mice (out of a possible ten) in which the test compound produced analgesia. The test compound was rated active if the number of writhes in the drug treatment group was significantly less than the number of writhes in the saline treatment group as determined by a one-way analysis of variance. If the initial test done of 10 mg/kg inhibited writhing in greater than 6 of 10 mice, the effect of additional doses was evaluated and an $ED_{50}$ value was calculated using a maximum likelihood function.

Opiate Binding Assay

The test compounds were evaluated from their ability to displace the binding of $^3$H-Naloxone to opiate receptors isolated from rat brain. Male rat [Crl: CD(SD) BR] obtained from Charles River Laboratories (Portage, MI) were sacrificed by cervical dislocation. A purified homogenate of receptor membranes was prepared from the brains according to the method described by Chang and Cuatrecasas. (K.-J. Chang and P. Cuatrecasas. Multiple Opiate Receptors: Enkephalins And Morphine Bind To Receptors Of Different Specificity. *J. Biol. Chem.* 254, 2610–2618 (1979).) The brains were homogenized in 10 volumes of 0.32M sucrose and centrifuged twice at 6,000×g for 15 minutes. Following centrifugation of the supernatants at 40,000×g for 30 minutes, the pellets were resuspended in 5 mM tris HCl, and centrifuged at 6,000×g. The supernatant was centrifuged at 40,000×g. The resuspension in 5 mM tris and centrifugation was repeated twice. The final pellet was resuspended in 2 volumes of 50 mM tris HCl (pH 7.4). The homogenate was assayed for protein content according to the method of Itzhaki and Gill (R. F. Itzhaki and D. M. Gill, A Micro-Biuret Method For Estimating Proteins. *Anal. Biochem.* 9, 401–410 (1964).)

The binding of the test compounds to the receptor membrane preparation was measured using a modification of the method of Pert and Snyder (C. B. Pert and S. H. Snyder, Properties Of Opiate-Receptor Binding In Rat Brain. *Proc. Natl. Acad. Sci.* 70, 2243–2247 (1973).) The receptor assay was run using a final concentration of 1 nM $^3$H-Naloxone and 0.5 mg/ml of homogenate protein. Levorphanol ($1\times10^{-5}$M) was used as the displacer for non-specific binding. The final concentration of the test compound was $10^{-5}$M. The assay was run in 0.05M tris HCl (pH 7.4). Total assay volume was 1.0 ml. Samples were incubated at 24° C. for 60 min., filtered over Whatman GF/C glass fiber filters, and rinsed twice with 2.4 ml washes of ice-cold buffer. The filters were air dried at 50° C. for 30 min. After drying, 10 ml. of PCS was added to the vial and radioactivity determined using a Tracor Analytic Mark III liquid scintillation counter with a counting efficiency of 48%.

The $IC_{50}$ values, i.e., the concentration of the test compounds which inhibited $^3$H-Naloxone specific binding to the opiate receptor by 50%, were obtained from log-logit plots of concentration-response curves.

The compounds of the present invention as represented by Formula I can be administered in such oral dosage forms as tablets, capsules, pills, powders, granules, suspensions, or solutions. They may also be administered rectally or vaginally, in such forms as suppositories or bougies. They may also be introduced in the form of eye drops, or they may be administered intraperitoneally, subcutaneously, or intramuscularly, using forms known to the pharmaceutical art. In general, the preferred route of administration is oral.

An effective but nontoxic quantity of the compound is employed in treatment. The dosage regimen for preventing or treating symptoms by the compounds of this invention is selected in accordance with a variety of factors including the type, age, weight, sex and medical condition of the mammal, the severity of the symptoms, and the route of administration of the particular compound employed. A physician or veterinarian of ordinary skill will readily determine and prescribe the therapeutically effective dosage based on the route of administration of the analgesic agent to prevent or arrest the progress of the condition. In so proceeding, the physician or veterinarian could employ relatively low dosages at first, subsequently increasing the dose until a maximum response is obtained.

The compounds of Formula I can also be administered as pharmaceutically acceptable acid addition salts such as the hydrochloride, hydrobromide, hydroiodide, sulfate, phosphate, acetate, propionate, lactate, maleate, malate, succinate, tartrate and the like. Additionally, the compounds of this invention may be administered in a suitable hydrated form.

The compounds of this invention may be prepared by any number of methods known to those skilled in the art. For example, the particular sequence of reactions by which the individual amino acids are joined to form the compounds of Formula I is generally not of critical importance, being chosen principally for convenience or for maximum yields. Moreover, the choice of activating reagents and conditions for joining amino acids or small peptides is not limited to those specifically described herein. The peptide intermediates and products of this invention are typically purified by crystallization or by column chromatography. Column chromatography also permits the separation of diastereomeric pairs into the individual diastereomers, thereby allowing one to employ a racemic amino acid as a starting material in the dipeptide synthesis.

The accompanying examples illustrate the methods used to prepare the compounds of this invention. These examples are given by way of illustration only and in no way should be construed as limiting the invention in spirit or in scope, as many modifications in materials and methods will be apparent from this disclosure to those skilled in the art.

DESCRIPTION OF THE PREFERRED EMBODIMENT

Example 1

1-[(1,1-dimethylethoxy)carbonyl]-N-(3-phenylpropyl)-2S-pyrrolidinecarboxamide

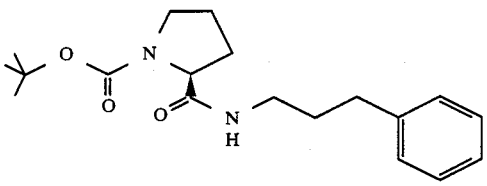

(Boc—(L)Pro—NH(CH$_2$)$_3$Ph)
Boc = t-butoxylcarbonyl
Ph = phenyl

To 8.17 g of Boc-L-proline (38.0 mmol) dissolved in 70 ml of CH$_2$Cl$_2$ and cooled to 0° C. was added 5.0 ml of N-methyl-morpholine (45.6 mmol). The resulting solution was cooled to −78° C. while being stirred vigorously under an argon atmosphere and 59 ml of isobutylchloroformate (45.6 mmol) were added. The reaction was then allowed to slowly warm to 0° C. before it was again cooled to −78° C. and charged with 6.2 g of 3-phenyl-1-aminopropane (45.6 mmol). The reaction mixture was warmed to room temperature, stirred for 24 h and then filtered. After diluting the filtrate with CH$_2$Cl$_2$, the filtrate was washed with 0.5N KHSO$_4$. The combined aqueous washes were extracted with CH$_2$Cl$_2$ and the combined organic layers were washed with brine, dried (Na$_2$SO$_4$), and stripped of all solvents. The residue titled product was dried under vacuum and used in subsequent reactions without further purification.

Optical Rotation [α]$_D$=−69.3°; −273.8° (365 nm)CHCl$_3$.

Analysis for C$_{19}$H$_{28}$N$_2$O$_3$ (MW=332.45): Calcd: C, 67.73; H, 8.52; N, 8.31. Found: C, 67.52; H, 8.49; N, 7.98.

Example 2

N-(3-phenylpropyl)-2S-pyrrolidinecarboxamide

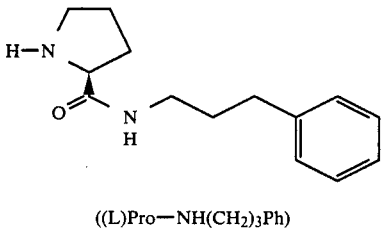

((L)Pro—NH(CH$_2$)$_3$Ph)

The product of Example 1 was dissolved in 50 ml of acetic acid to which was added 13 ml (a 10 fold excess) of 6.0N HCl/dioxane. The resulting solution was gently stirred under nitrogen at room temperature for 1 hour before all solvents was removed under reduced pressure to produce an oil. The oil solidified on treatment with diethyl ether. The salt was then suction filtered, washed with diethyl ether, and then dissolved in a mixture of 5% aqueous NaHCO$_3$ and CH$_2$Cl$_2$ in which there was sufficient NaHCO$_3$ solution to give a final aqueous pH of 8.0. The organic layer was separated, washed with brine, dried (Na$_2$SO$_4$), and stripped of all solvent under reduced pressure to give the title material as a viscous oil.

Optical Rotation [α]$_D$−54.9°; −145.1° (365 nm)CHCl$_3$.

Analysis for C$_{14}$H$_{20}$N$_2$O.½H$_2$O (MW=234.58): Calcd: C, 71.68; H, 8.70; N, 11.94. Found: C, 71.71; H, 8.76; N, 12.04.

Example 3

N-[(1,1-dimethylethoxy)carbonyl]-2,6-dimethyl-D,L-tyrosyl-N-(3-phenylpropyl)-L-prolinamide

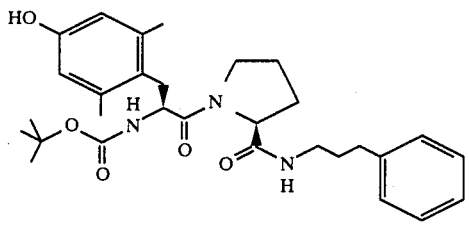

mixture of diastereomers (Boc—2,6-Me$_2$—(D,L)Tyr—(L)Pro—NH(CH$_2$)$_3$Ph)

To 60 mmol (18.5 g) of racemic 2,6-dimethyltyrosine in 150 ml of CH$_2$Cl$_2$ cooled to 0° C. under an argon atmosphere was added 60 mmol (6.6 ml) of N-methylmorpholine. After cooling this vigorously stirred solution to −78° C., 60 mmol (7.9 ml) of isobutylchloroformate were added. The reaction mixture was allowed to warm up to 20° C. before it was again cooled to −78° C. and 60 mmol (14.1 g) of the product of Example 2, (L)-Pro-NH(CH$_2$)$_3$Ph, was added to the reaction mixture in a single portion. The mixture was allowed to warm to room temperature and stirred for an additional 18 hours. The reaction mixture was then filtered through diatomaceous earth and the filtrate was washed 3× with 100 ml of 0.5N KHSO$_4$. After extracting the combined aqueous washes with 100 ml of CH$_2$Cl$_2$, the combined organic extract and filtrate was washed with 100 ml of brine, dried (Na$_2$SO$_4$) and stripped of all solvent under reduced pressure to produce the title product as a mixture of diastereomers. The two diastereomers were separated by pressure liquid chromatography.

Diastereomer A

Optical Rotation [α]$_D$−34.0°; −17.9° (365 nm)CHCl$_3$.

Analysis for C$_{30}$H$_{41}$N$_3$O$_5$ (MW=523.68): Calcd: C, 68.81; H, 7.89; N, 8.02. Found: C, 68.90; H, 7.80; N, 8.19.

Diastereomer B

Optical Rotation [α]$_D$−78.3°; −374.8° (365 nm)CHCl$_3$.

Analysis for C$_{30}$H$_{41}$N$_3$O$_5$ (MW=523.68): Calcd: C, 68.81; H, 7.89; N, 8.02. Found: C, 68.90; H, 7.80; N, 8.19.

Example 4

2,6-dimethyltyrosyl-N-(3-phenylpropyl)-L-prolinamide, monohydrochloride

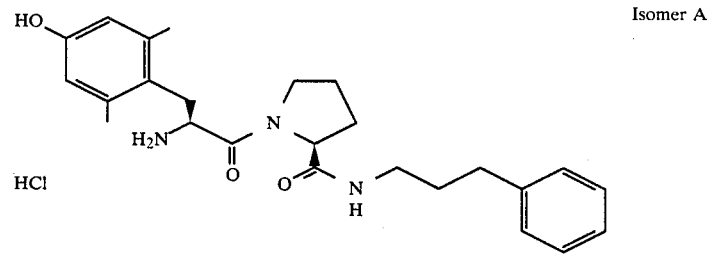

Isomer A (2,6-Me$_2$Tyr(L)Pro—NH(CH$_2$)$_3$Ph.HCl

Diastereomer A of Example 3 was dissolved in 50 ml of acetic acid to which was added 13 ml (a 10 fold molar excess) of 6.0N HCl/dioxane. The resulting solution was gently stirred under nitrogen at room temperature for 1 hour before all solvent was removed under reduced pressure to produce an oil, which solidified upon treatment with diethyl ether. The solid (salt) was suction filtered, washed with diethyl ether, and dried under vacuum.

Optical Rotation [α]$_D$+16.4°; +58.4° (365 nm)CH$_3$OH.

Analysis for C$_{25}$H$_{34}$N$_3$O$_3$Cl.½H$_2$O (MW=469.03): Calcd: C, 64.02; H, 7.52; N, 8.95; Cl, 7.56. Found: C, 63.84; H, 7.31; N, 8.86; Cl, 7.74.

Example 5

2,6-dimethyltyrosyl-N-(3-phenylpropyl)-L-prolinamide, monohydrochloride

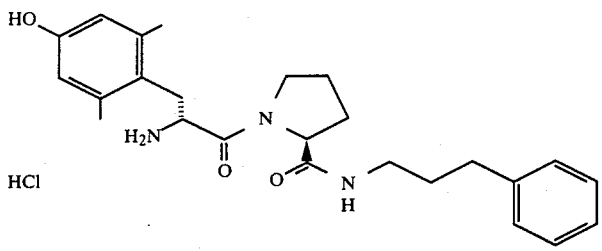

(2,6-Me$_2$Tyr—(L)Pro—NH(CH$_2$)$_3$Ph.HCl)

The title compound, the hydrochloride salt of diastereomer B of Example 3, was prepared according to the method of Example 4.

Optical Rotation [α]$_D$−153.6°; −550.6° (365 nm)CH$_3$OH.

Analysis for C$_{25}$H$_{34}$N$_3$O$_3$Cl.½H$_2$O (MW=469.03): Calcd: C, 64.02; H, 7.52; N, 8.95; Cl, 7.56. Found: C, 63.72, H, 7.46; N, 8.87; Cl, 7.62.

Example 6

N-(3-phenylpropyl)-2R-pyrrolidinecarboxamide

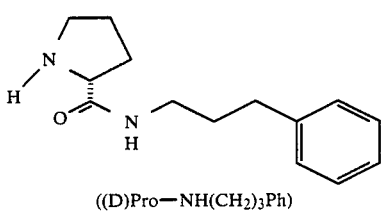

((D)Pro—NH(CH$_2$)$_3$Ph)

The Boc precursor of the title compound was prepared by the method of Example 1 using Boc-D-proline in place of Boc-L-proline. The Boc precursor was then hydrolyzed and converted to the free base (title compound) by the method of Example 2.

Optical Rotation [α]$_D$+63.1°; +191.0° (365 nm)(CH$_3$OH.

Analysis for C$_{14}$H$_{20}$N$_2$O.⅛H$_2$O (MW=234.58): Calcd: C, 71.68; H, 8.70; N, 11.94. Found: C, 71.89; H, 8.47; N, 12.00.

Example 7

Mixture of
N-[(1,1-dimethylethoxy)carbonyl]-2,6-dimethyl-D-tyrosyl-N-(3-phenylpropyl)-D-prolinamide and
N-[(1,1-dimethylethoxy)carbonyl]-2,6-dimethyl-L-tyrosyl-N-(3-phenylpropyl)-D-prolinamide

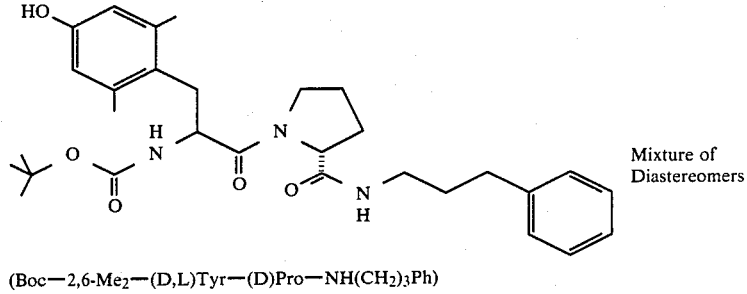

(Boc—2,6-Me$_2$—(D,L)Tyr—(D)Pro—NH(CH$_2$)$_3$Ph)

The title mixture of diastereomers (isomers A+B) was prepared by the method of Example 3 using the product of Example 6, (D)Pro-NH(CH$_2$)$_3$Ph, in place of (L)Pro-NH(CH$_2$)$_3$Ph. The title product as a mixture of diastereomers was separated into isomers A and B by pressure liquid chromatography.

Diastereomer A

Optical Rotation [α]$_D$+106.4°; +413.6° (365 nm)CHCl$_3$.

Analysis for C$_{30}$H$_{41}$N$_3$O$_5$ (MW=523.68): Calcd: C, 68.81; H, 7.89; N, 8.02. Found: C, 68.70; H, 7.89; N, 7.99.

Diastereomer B

Optical Rotation [α]$_D$+6.7°; +66.7° (365 nm)CHCl$_3$.

Analysis for C$_{30}$H$_{41}$N$_3$O$_5$.¼H$_2$O (MW=528.17): Calcd: C, 68.22; H, 7.92; N, 7.95. Found: C, 67.96; H, 7.84; N, 8.11.

Example 8
2,6-dimethyltyrosyl-N-(3-phenylpropyl)-D-prolinamide, monohydrochloride

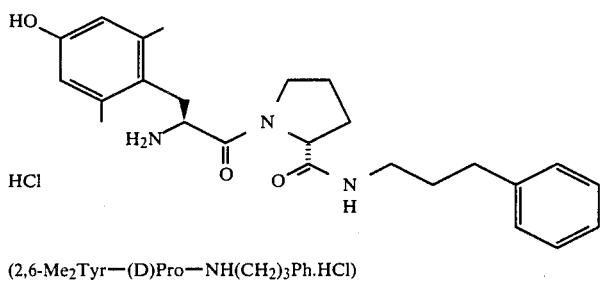

(2,6-Me₂Tyr—(D)Pro—NH(CH₂)₃Ph.HCl)

The title compound was prepared from diastereomer A of Example 7 by the method of Example 4.

Optical Rotation [α]$_D$ −2.7°; −31.8° (365 nm)CH₃OH.

Analysis for C₂₅H₃₄N₃O₃Cl.¾H₂O (MW=473.52): Calcd: C, 63.41; H, 7.56; Cl, 7.49. Found: C, 63.22; H, 7.43; Cl, 7.96.

Example 9
2,6-dimethyltyrosyl-N-(3-phenylpropyl)-D-prolinamide, monohydrochloride

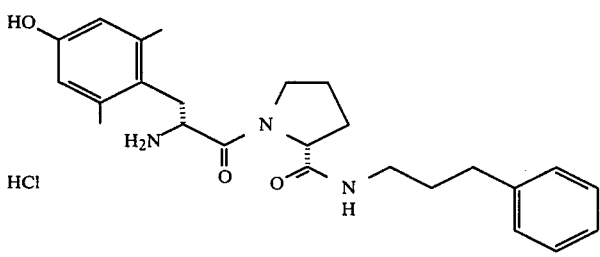

(2,6-Me₂Tyr—(D)Pro—NH(CH₂)₃Ph.HCl)

The title compound was prepared from diastereomer B of Example 7 by the method of Example 4.

Optical Rotation [α]$_D$ +40.0°; +440.9° (365 nm)CH₃OH

Analysis for C₂₅H₃₄N₃O₃Cl.¼H₂O (MW=464.52): Calcd: C, 64.64; H, 7.48; N, 9.05; Cl, 7.63. Found: C, 64.50; H, 7.37; N, 9.08; Cl, 7.62.

Example 10
1-[[(1,1-dimethylethoxy)carbonyl]amino]-N-(3-phenylpropyl)cyclobutanecarboxamide

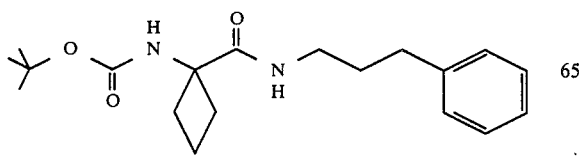

(Boc—NHspiroC₄Gly—NH(CH₂)₃Ph)

The title compound is prepared by the method of Example 1 using Boc-glycine spirobutyl in place of Boc-L-proline.

Example 11
1-amino-N-(3-phenylpropyl)cyclobutanecarboxamide, monohydrochloride

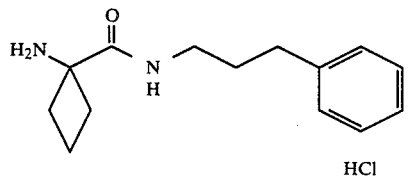

(NH₂spiroC₄Gly—NH(CH₂)₃Ph.HCl)

The title compound is prepared by the method of Example 4 using the title material from Example 10.

Example 12

(±)α-[[(1,1-dimethylethoxy)carbonyl]amino]-4-hydroxy-2,6-dimethyl-N-[1-[[(3-phenylpropyl)amino]carbonyl]cyclobutyl]benzenepropanamide

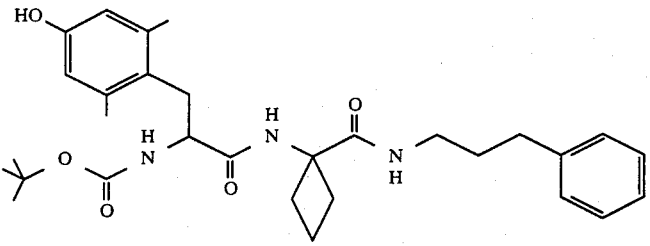

(Boc—Me₂—(D,L)Tyr—NHspiroC₄Gly—NH(CH₂)₃Ph)

The title compound is prepared by the method of Example 2 using the title compound from Example 11, NH₂spiroC₄Gly-NH(CH₂)₃Ph HCl, in place of (L)Pro-NH(CH₂)₃Ph.

Example 13

(±)α-amino-4-hydroxy-2,6-dimethyl-N-[1-[[(3-phenylpropyl)amino]carbonyl]cyclobutyl]benzenepropanamide, monohydrochloride

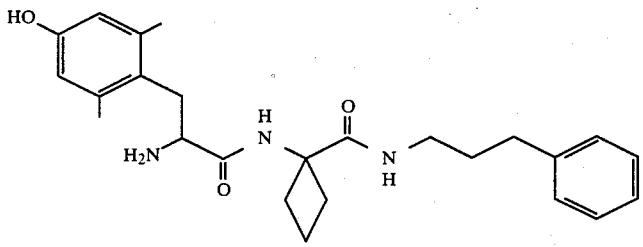

HCl
(2,6-Me₂—(D,L)Tyr—NHspiroC₄Gly—NH(CH₂)₃Ph.HCl)

The title compound is prepared by the method of Example 4 from the title compound of Example 12.

Example 14

1-amino-N-(3-phenylpropyl)cyclopentanecarboxamide, monohydrochloride

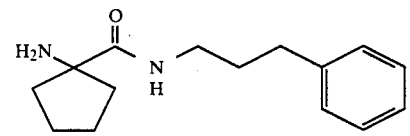

HCl (NH₂spiroC₅Gly—NH(CH₂)₃Ph.HCl)

The Boc precursor of the title material was prepared by the method of Example 1 using Boc-spiropentyl glycine in place of Boc-L-proline. The title compound was generated from the Boc precursor by the method of Example 4.

Analysis for C₁₅H₂₃N₂OCl (MW=282.81): Calcd: C, 63.71; H, 8.20; N, 9.91; Cl, 12.54. Found: C, 63.36; H, 8.35; N, 9.78; Cl, 12.74.

Example 15

(±)α-[[(1,1-dimethylethoxy)carbonyl]amino]-4-hydroxy-2,6-dimethyl-N-[1-[[(3-phenylpropyl)amino]carbonyl]cyclopentyl]benzenepropanamide

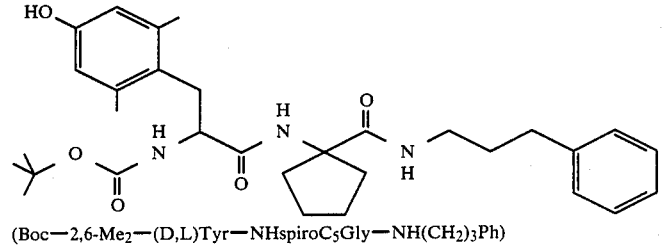

(Boc—2,6-Me₂—(D,L)Tyr—NHspiroC₅Gly—NH(CH₂)₃Ph)

The title compound was prepared by the method of Example 3 using the title compound from Example 14, NH₂spiroC₅Gly-NH(CH₂)₃Ph.HCl, in place of (L)Pro-NH(CH₂)₃Ph.

Analysis for C₃₁H₄₃N₃O₅ (MW=537.70): Calcd: C, 69.19; H, 8.06; N, 7.81. Found: C, 69.06; H, 8.17; N, 7.74.

Example 16

(±)α-amino-4-hydroxy-2,6-dimethyl-N-[1-[[(3-phenyl-propyl)amino]carbonyl]cyclopentyl]benzenepropanamide, monohydrochloride

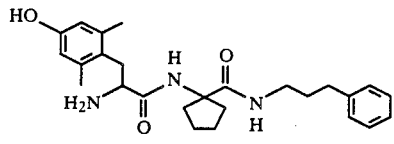

(2,6-Me₂—(D,L)Tyr—NHspiroC₅Gly—NH(CH₂)₃Ph.HCl)

The title compound was prepared by the method of Example 4 from the title compound of Example 15.

Analysis for C₂₆H₃₅N₃O₃.1⅛HCl.⅓H₂O (MW=487.60): Calcd: C, 64.16; H, 7.68; N, 8.63; Cl, 8.01. Found: C, 64.04; H, 7.67; N, 8.63; Cl, 8.18.

Example 17

1-amino-N-(3-phenylpropyl)cyclohexanecarboxamide, monohydrochloride

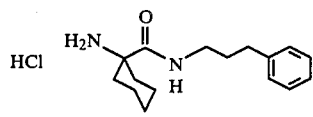

(NH₂—spiroC₆Gly—NH(CH₂)₃Ph.HCl)

The Boc precursor of the title compound was prepared by the method of Example 1 using Boc-spirohexyl glycine in place of Boc-L-proline. The title compound was then obtained from this Boc precursor by the method of Example 4.

Analysis for C₁₅H₂₃N₂OCl (MW=282.81): Calcd: C, 63.71; H, 8.20; N, 9.91; Cl, 12.54. Found: C, 63.36; H, 8.35; N, 9.78; Cl, 12.74.

Example 18

(±)α-[[(1,1-dimethylethoxy)carbonyl]amino]-4-hydroxy]2,6-dimethyl-N-[1-[[(3-phenylpropyl)amino]-carbonyl]cyclohexyl]benzenepropanamide

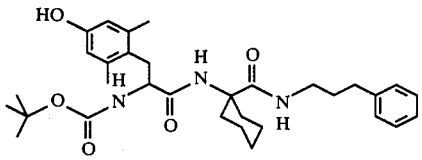

(Boc—2,6-Me₂—(D,L)Tyr—NHspiroC₆Gly—NH(CH₂)₃Ph)

The title compound was prepared by the method of Example 3 using the title compound of Example 17, NH₂-spiroC₆Gly-NH(CH₂)₃Ph.HCl, in place of (L)-Pro-NH(CH₂)₂Ph.

Analysis for C₃₂H₄₅N₃O₅ (MW=551.72): Calcd: C, 69.66; H, 8.22; N, 7.62. Found: C, 69.30; H, 8.28; N, 7.50.

Example 19

(±)α-amino-4-hydroxy-2,6-dimethyl-N-[1-[[(3-phenyl-propyl)amino]carbonyl]cyclohexyl]benzenepropanamide, monohydrochloride

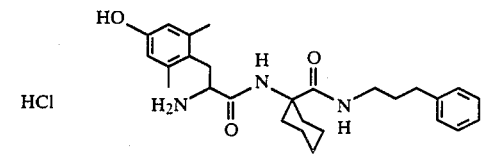

(2,6-Me₂—(D,L)Tyr—NHspiroC₆Gly—NH(CH₂)₃Ph.HCl)

The title compound was prepared by the method of Example 4 from the title compound of Example 18.

Analysis for C₂₇H₃₇N₃O₃.1⅛HCl.H₂O (MW=510.64): Calcd: C, 63.51; H, 7.92; N, 8.23; Cl, 7.81. Found: C, 63.62; H, 7.75; N, 8.16; Cl, 7.97.

Example 20

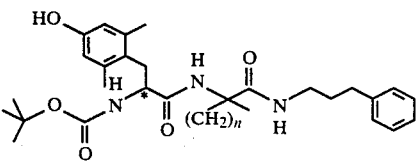

n = 3, 4, or 5
* = L or D n=3, D
αR-[[(1,1-dimethylethoxy)carbonyl]amino]-4-hydroxy-2,6-dimethyl-N-[1-[[(3-phenylpropyl)amino]carbonyl]cyclobutyl]benzenepropanamide, monohydrochloride n=3, L
αS-[[(1,1-dimethylethoxy)carbonyl]amino]-4-hydroxy-2,6-dimethyl-N-[1-[[(3-phenylpropyl)amino]carbonyl]cyclobutyl]benzenepropanamide, monohydrochloride n=4, D
αR-[[(1,1-dimethylethoxy)carbonyl]amino]-4-hydroxy-2,6-dimethyl-N-[1-[[(3-phenylpropyl)amino]carbonyl]cyclopentyl]benzenepropanamide, monohydrochloride n=4, L
αS-[[(1,1-dimethylethoxy)carbonyl]amino]-4-hydroxy-2,6-dimethyl-N-[1-[[(3-phenylpropyl)amino]carbonyl]cyclopentyl]benzenepropanamide, monohydrochloride n=5, D
αR-[[(1,1-dimethylethoxy)carbonyl]amino]-4-hydroxy-2,6-dimethyl-N-[1-[[(3-phenylpropyl)amino]carbonyl]cyclohexyl]benzenepropanamide, monohydrochloride n=5, L
α-S-[[(1,1-dimethylethoxy)carbonyl]amino]-4-hydroxy-2,6-dimethyl-N-[1-[[(3-phenylpropyl)amino]carbonyl]cyclohexyl]benzenepropanamide, monohydrochloride The title compounds are prepared by the method of Example 3 using the title materials from Examples 11, 14, or 18 in place of (L)-Pro-NH(CH₂)₃Ph and either Boc-2,6-Me₂(L)Tyr or Boc-2,6-Me₂-(D)Tyr in place of Boc-2,6-Me₂-(D,L)Tyr.

Example 21

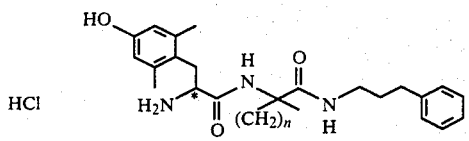

n = 3, 4, or 5
\* = L or D n=3, D
αR-amino-4-hydroxy-2,6-dimethyl-N-[1-[[(3-phenyl-propyl)amino]carbonyl]cyclobutyl]benzenepropana-mide, monohydrochloride n=3, L
αS-amino-4-hydroxy-2,6-dimethyl-N-[1-[[(3-phenyl-propyl)amino]carbonyl]cyclobutyl]benzenepropana-mide, monohydrochloride n=4, D
αR-amino-4-hydroxy-2,6-dimethyl-N-[1-[[(3-phenyl-propyl)amino]carbonyl]cyclopentyl]benzene-propanamide, monohydrochloride n=4, L
αS-amino-4-hydroxy-2,6-dimethyl-N-[1-[[(3-phenyl-propyl)amino]carbonyl]cyclopentyl]benzene-propanamide, monohydrochloride n=5, D
αR-amino-4-hydroxy-2,6-dimethyl-N-[1-[[(3-phenyl-propyl)amino]carbonyl]cyclohexyl]benzenepropana-mide, monohydrochloride n=5, L
αS-amino-4-hydroxy-2,6-dimethyl-N-[1-[[(3-phenyl-propyl)amino]carbonyl]cyclohexyl]benzenepropana-mide, monohydrochloride The title compounds are prepared by the method of Example 4 from the products of Example 20.

What is claimed is:
1. A compound of the formula:

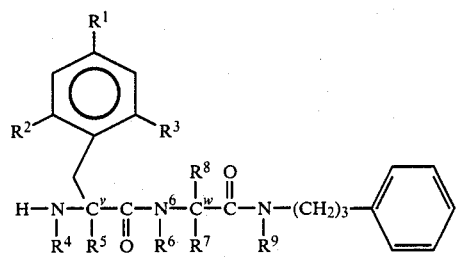

and the pharmaceutically acceptable addition salts thereof, wherein $R_1$ is —OH or —OCH$_3$; wherein $R^2$ and $R^3$ may be the same or different and represent straight or branched chain lower alkyl of 1-6 carbon atoms; wherein $R^4$, $R^5$ and $R^9$ may be the same or different and represent hydrogen or straight or branched chain lower alkyl having 1-6 carbon atoms; wherein $R^6$ represents hydrogen, or straight or branched chain lower alkyl of 1-6 carbon atoms, or $R^6$ may act together with $N^6$, $C^w$ and either $R^7$ or $R^8$ to form a cycloamine of the formula:

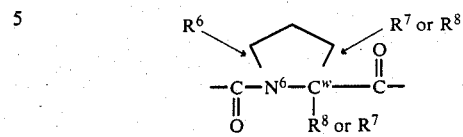

such that between $R^7$ and $R^8$, when one acts to form said cycloamine, the other is hydrogen, or straight or branched chain lower alkyl of 1-6 carbon atoms; wherein when neither $R^7$ nor $R^8$ is acting to form said cycloamine, then $R^7$ and $R^8$ act together with $C^w$ to form a cycloalkyl of the formula:

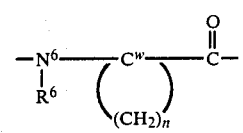

where n=3, 4, 5; wherein $C^w$ represents an asymmetric carbon atom when $R^7$ and $R^8$ are not the same and may be racemic or have the D or L configuration; and wherein $C^v$ represents an asymmetric carbon atom that may be racemic or that may have the D or L configuration.

2. A compound according to claim 1 of the formula:

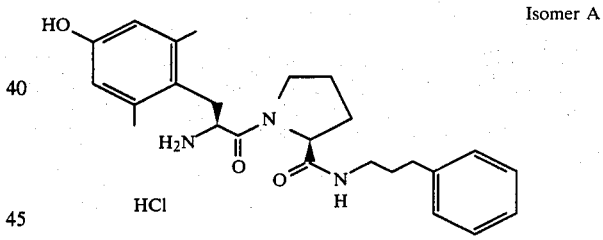

2,6-dimethyltyrosyl-N-(3-phenylpropyl)-L-prolina-mide, monohydrochloride.

3. A compound according to claim 1 of the formula:

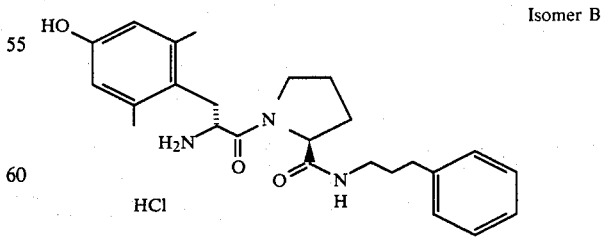

2,6-dimethyltyrosyl-N-(3-phenylpropyl)-L-prolina-mide, monohydrochloride.

4. A compound according to claim 1 of the formula:

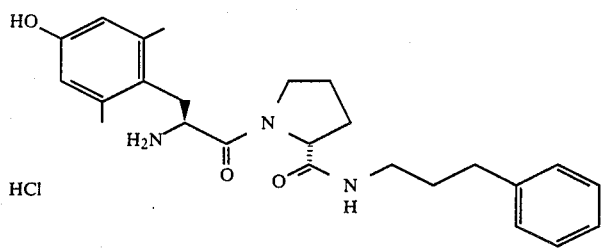

2,6-dimethyltyrosyl-N-(3-phenylpropyl)-D-prolinamide, monohydrochloride.

5. A compound according to claim 1 of the formula:

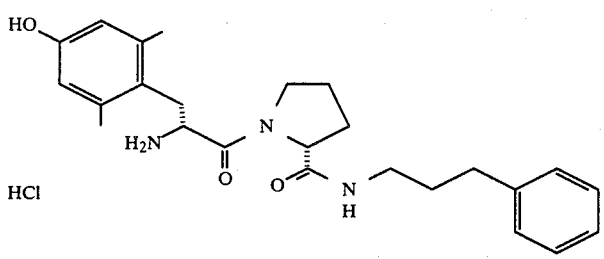

2,6-dimethyltyrosyl-N-(3-phenylpropyl)-D-prolinamide, monohydrochloride.

6. A compound according to claim 1 of the formula:

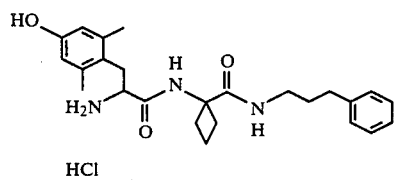

(±)α-amino-4-hydroxy-2,6-dimethyl-N-[1-[[(3-phenylpropyl)amino]carbonyl]cyclobutyl]benzenepropanamide, monohydrochloride.

7. A compound according to claim 1 of the formula:

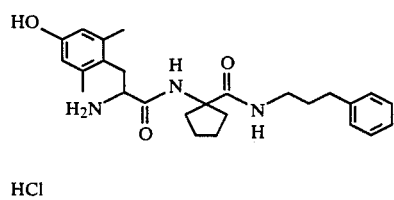

(±)α-amino-4-hydroxy-2,6-dimethyl-N-[1-[[(3-phenylpropyl)amino]carbonyl]cyclopentyl]benzenepropanamide, monohydrochloride.

8. A compound according to claim 1 of the formula:

Isomer A

Isomer B

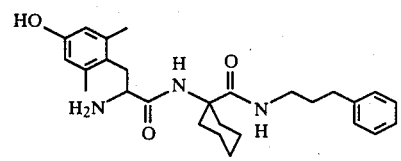

(±)α-amino-4-hydroxy-2,6-dimethyl-N-[1-[[(3-phenylpropyl)amino]carbonyl]cyclohexyl]benzenepropanamide, monohydrochloride.

9. A compound according to claim 1 of the formula:

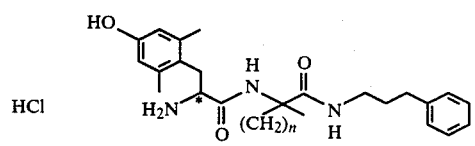

wherein n=2, 3 or 4; and wherein * is D or L or racemic.

10. A compound according to claim 1 of the formula:

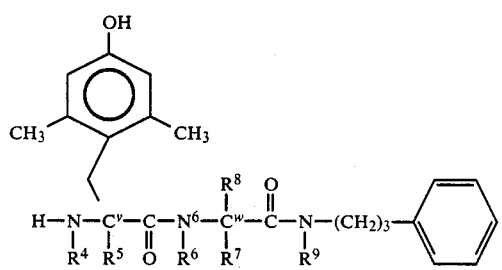

wherein $R^4$, $R^5$, and $R^6$ may be the same or different and represent hydrogen or straight or branched chain lower alkyl having 1-6 carbon atoms; wherein $R^6$ represents hydrogen, or straight or branched chain lower alkyl of 1-6 carbon atoms, or $R^6$ may act together with $N^6$, $C^w$ and either $R^7$ and $R^8$ to form a cycloamine of the formula:

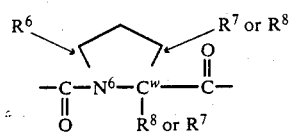

such that between $R^7$ and $R^8$, when one acts to form said cycloamine, the other is hydrogen, or straight or branched chain lower alkyl of 1-6 carbon atoms; wherein when neither $R^7$ nor $R^8$ is acting to form said cycloamine, then $R^7$ and $R^8$ act together with $C^w$ to form a cycloalkyl of the formula:

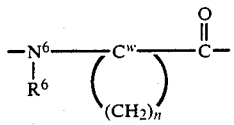

where n=3,4, 5; wherein $C^w$ represents an asymmetric carbon atom when $R^7$ and $R^8$ are not the same and may be racemic or have the D or L configuration; and wherein $C^v$ represents an asymmetric carbon atom that may be racemic or that may have the D or L configuration.

* * * * *

UNITED STATES PATENT AND TRADEMARK OFFICE
CERTIFICATE OF CORRECTION

PATENT NO. : 4,767,744

DATED : August 30, 1988

INVENTOR(S) : Hansen, Jr. et al.

Page 1 of 2

It is certified that error appears in the above-identified patent and that said Letters Patent is hereby corrected as shown below:

On the front page of the patent and Column 1, lines 1-2, reading "SUBSTITUTED TYROSYL METHIONYL DIPEPTIDE AMIDES" should read -- CONFORMATIONALLY RESTRICTED TYROSYL DIPEPTIDE AMIDES --.

On the front page of the patent, in the Abstract, line 27 (the line above the second structure in the second column), reading "$R^7R^8$" should read -- $R^7$ or $R^8$ --.

On the front page of the patent, line 38 (two lines above the third structure in the second column), reading "$R^7R^8$" should read -- $R^7$ and $R^8$ --.

Column 16, line 14, reading "-NHspiro$C_5$Gly-" should read -- -NHspiro$C_6$Gly- --.

UNITED STATES PATENT AND TRADEMARK OFFICE
CERTIFICATE OF CORRECTION

PATENT NO. : 4,767,744
DATED : August 30, 1988
INVENTOR(S) : Hansen, Jr. et al.

It is certified that error appears in the above-identified patent and that said Letters Patent is hereby corrected as shown below:

Column 20, line 62, reading "$R^6$" should read -- $R^9$ --.

Column 20, line 67, reading "$R^7$ and $R^8$" should read -- $R^7$ or $R^8$ --.

Signed and Sealed this

Tenth Day of July, 1990

*Attest:*

HARRY F. MANBECK, JR.

*Attesting Officer*     Commissioner of Patents and Trademarks